(12) United States Patent
Higashino

(10) Patent No.: US 12,329,793 B2
(45) Date of Patent: Jun. 17, 2025

(54) MODIFIED ADENOVIRUS AND MEDICINE COMPRISING SAME

(71) Applicant: National University Corporation Hokkaido University, Sapporo (JP)

(72) Inventor: Fumihiro Higashino, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 938 days.

(21) Appl. No.: 17/439,184

(22) PCT Filed: Mar. 19, 2020

(86) PCT No.: PCT/JP2020/012196
§ 371 (c)(1),
(2) Date: Sep. 14, 2021

(87) PCT Pub. No.: WO2020/189749
PCT Pub. Date: Sep. 24, 2020

(65) Prior Publication Data
US 2022/0152133 A1   May 19, 2022

(30) Foreign Application Priority Data

Mar. 20, 2019 (JP) .................... 2019-053895

(51) Int. Cl.
*A61K 35/761* (2015.01)
*A61P 29/00* (2006.01)
*A61P 35/00* (2006.01)

(52) U.S. Cl.
CPC .......... *A61K 35/761* (2013.01); *A61P 29/00* (2018.01); *A61P 35/00* (2018.01)

(58) Field of Classification Search
CPC .............. A61K 35/761; C12N 15/86; C12N 2710/10332; A61P 29/00; A61P 35/00
See application file for complete search history.

(56) References Cited

U.S. PATENT DOCUMENTS

| | | | |
|---|---|---|---|
| 6,844,192 B2 * | 1/2005 | Orlando et al. ......... | C12N 5/10 |
| 9,718,863 B2 * | 8/2017 | Colloca et al. ........ | C07K 14/005 |
| 2006/0121000 A1 | 6/2006 | Vile et al. | |
| 2007/0298498 A1 * | 12/2007 | Colloca et al. ......... | C12N 15/86 |
| 2013/0302313 A1 | 11/2013 | Yu et al. | |
| 2015/0374766 A1 | 12/2015 | O'Shea et al. | |

FOREIGN PATENT DOCUMENTS

| | | | |
|---|---|---|---|
| EP | 1112371 B2 * | 10/1999 | ............. C12N 15/86 |
| EP | 1112371 B1 | 7/2001 | |
| JP | 2016-160249 A * | 9/2016 | |
| WO | 0015820 A1 | 3/2000 | |
| WO | 2004042015 A2 | 5/2004 | |
| WO | 2014153204 A1 | 9/2014 | |

OTHER PUBLICATIONS

International Preliminary Report on Patentability Chapter II (translation) for PCT/JP2020/012196, Sep. 20, 2021.*
Mikawa et al., Conditionally Replicative Adenovirus Controlled by the Stabilization System of AU-Rich Elements Containing mRNA, (2020), Cancers 12, 1205, (Year: 2020).*
Human Adenovirus Ad5 sequence alignment with SEQ ID No. 1 (2007).*
Mastadenovirus—Adenoviridae sequence alignment with SEQ ID No. 2 (2009).*
Extended European Search Report for European Application No. 20774238.8, dated Apr. 6, 2023, 7 pages.
Taiwanese Office Action for Taiwanese Application No. 109109287, dated Feb. 21, 2023 with partial translation, 9 pages.
Ahmed et al., "A conditionally replicating adenovirus targeted to tumor cells through activated RAS/P-MAPK-selective mRNA stabilization", Nature Biotechnology, 2003, vol. 21, No. 7, pp. 771-777.
Bischoff et al., "An adenovirus mutant that replicates selectively in p53-deficient human tumor cells", Science, 1996, vol. 274, No. 4, pp. 373-376.
Dixon et al., "Post-transcriptional Control of Cyclooxygenase-2 Gene Expression", Journal of Biological Chemistry, 2000, vol. 275, No. 16, pp. 11750-11757.
Eloit et al., "Isogenic adenoviruses type 5 expressing or not expressing the E1A gene: efficiency as virus vectors in the vaccination of permissive and non-permissive species", Journal of General Virology, 1995, 76, pp. 1583-1589.
Ganly et al., "A phase I study of Onyx-015, an E1B attenuated adenovirus, administered intratumorally to patients with recurrent head and neck cancer", Clinical Cancer Research, 2000, vol. 6, pp. 798-806.
Halbert et al., "Adenovirus early region 4 encodes functions required for efficient DNA replication, late gene expression, and host cell shutoff", Journal of Virology, 1985, vol. 56, No. 1, pp. 250-257.

(Continued)

*Primary Examiner* — Valarie E Bertoglio
(74) *Attorney, Agent, or Firm* — Buchanan Ingersoll & Rooney PC

(57) ABSTRACT

[Problem] The purpose of the present invention is to provide a modified adenovirus having a cytocidal activity on a target cell and high safety.
[Solution] The present invention pertains to: a modified adenovirus which comprises an E1A gene, an enhancer sequence having a function of enhancing the expression of the E1A gene, and an AU-rich element introduced into the 3'-untranslated region of a viral gene, which is essentially required for the self-propagation thereof, or a position adjacent to the 3'-untranslated region, or a modified adenovirus which comprises an E1A gene and an enhancer sequence having a function of enhancing the expression of the E1A gene and cannot express normal E4orf6 protein, wherein the distance between the 5'-terminus of the E1A gene and the terminus of the enhancer sequence is 1500-4500 bp; and a medicine comprising the same.

12 Claims, 3 Drawing Sheets
Specification includes a Sequence Listing.

(56) References Cited

OTHER PUBLICATIONS

Hasegawa et al., "HuR is exported to the cytoplasm in oral cancer cells in a different manner from that of normal cells" British Journal of Cancer, 2009, vol. 100, pp. 1943-1948.
Hearing et al., "The adenovirus type 5 E1A enhancer contains two functionally distinct domains: One is specific for E1A and the other modulates all early units in cis", Cell, 1986, 45, pp. 229-236.
Higashino et al., "Adenovirus E4orf6 targets pp32/LANP to control the fate of ARE-containing mRNAs by perturbing the CRM1-dependent mechanism", Journal of Cell Biology, 2005, vol. 170, No. 1, pp. 15-20.
International Preliminary Report on Patentability for International Application No. PCT/JP2020/012196, dated Mar. 5, 2021, 14 pages.
International Search Report and Written Opinion for International Application PCT/JP2020/012196, dated Jun. 16, 2020, 7 pages.
Kakuguchi et al., "HuR knockdown changes the oncogenic potential of oral cancer cells", Molecular Cancer Research, 2010, vol. 8, No. 4, pp. 520-528.
Khalid et al., "Post-transcriptional control during chronic inflammation and cancer: a focus on AU-rich elements", Cellular and Molecular Life Science, 2010, vol. 67, pp. 2937-2955.
Kuroshima et al., "Viral-mediated stabilization of AU-rich element containing mRNA contributes to cell transformation", Oncogene, 2011, vol. 30, pp. 2912-2920.
Lopez et al., "Role of the RNA-binding protein HuR in colon carcinogenesis", Oncogene, 2003, vol. 22, pp. 7146-7154.
Mikawa et al., "Conditionally replicative adenovirus controlled by the stabilization system of AU-rich elements containing mRNA", Cancers, 2020, 12, 1205, 13 pages.
Thiele et al., "AU-rich elements and alternative splicing in the β-catenin 3'UTR can influence the human β-catenin mRNA stability", Experimental Cell Research, 2006, vol. 312, No. 12, pp. 2367-2378.
Zamarin et al., "Oncolytic Newcastle Disease Virus for cancer therapy: old challenges and new directions", Future Microbiology, 2012, vol. 7, No. 3, pp. 347-367.
Chuan et al., "Tat PTD-Modified Oncolytic Adenovirus Driven by the SCG3 Promoter and ASH1 Enhancer for Neuroblastoma Therapy," Human Gene Therapy, Aug. 2013, vol. 24, pp. 766-775.

* cited by examiner

A.

B.

SEQUENCE LISTING

<160> NUMBER OF SEQ ID NOS: 9

<210> SEQ ID NO 1
<211> LENGTH: 871

```
<212> TYPE: DNA
<213> ORGANISM: Artificial Sequence
<220> FEATURE:
<223> OTHER INFORMATION: modified e4orf6 gene

<400> SEQUENCE: 1
atgactacgt ccggcgttcc atttggcatg acactacgac caacacgatc tcggttgtct    60
cggcgcactc cgtacagtag ggatcgtcta cctccttttg agacagaaac ccgcgctacc   120
atactggagg atcatccgct gctgcccgaa tgtaacactt tgacaatgca caacgtgagt   180
tacgtgcgag gtcttccctg cagtgtggga tttacgctga ttcaggaatg ggttgttccc   240
tgggatatgg ttctaacgcg ggaggagctt gtaatcctga ggaagtgtat gcacgtgtgc   300
ctgtgttgtg ccaacattga tatcatgacg agcatgatga tccatggtta cgagtcctgg   360
gctctccact gtcattgttc cagtcccggt tccctgcagt gtatagccgg cgggcaggtt   420
ttggccagct ggtttaggat ggtggtggat ggcgccatgt ttaatcagac gggaggtggt   480
gaattacaac atgccaaaag aggtaatgtt tatgtccagc gtgtttatga ggggtcgcca   540
cttaatctac ctgcgcttgt ggtatgatgg ccacgtgggt tctgtggtcc ccgccatgag   600
ctttggatac agccgccttg cactgtggga ttttgaacaat attgtggtgc tgtgctgcag   660
ttactgtgct gatttaagtg agatcagggt gcgctgctgt gcccggagga caaggcgcct   720
tatgctgcgg gcggtgcgaa tcatcgctga ggagaccact gccatgttgt attcctgcag   780
gacggagcgg cggcggcagc agtttattcg cgcgctgctg cagcaccacc gccctatcct   840
gatgcacgat tatgactcta cccccatgta g                                   871

<210> SEQ ID NO 2
<211> LENGTH: 294
<212> TYPE: PRT
<213> ORGANISM: Artificial Sequence
<220> FEATURE:
<223> OTHER INFORMATION: modified e4orf6 polypeptide

<400> SEQUENCE: 2

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
            35                  40                  45

Pro Glu Cys Asn Thr Leu Thr Met His Asn Val Ser Tyr Val Arg Gly
        50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Val Leu Ala Ser Trp
    130                 135                 140

Phe Arg Met Val Val Asp Gly Ala Met Phe Asn Gln Arg Ile Trp
145                 150                 155                 160

Tyr Arg Glu Val Val Asn Tyr Asn Met Pro Lys Glu Val Met Phe Met
                165                 170                 175
```

```
Ser Ser Val Phe Met Arg Gly Arg His Leu Ile Tyr Leu Arg Leu Trp
            180                 185                 190

Tyr Asp Gly His Val Gly Ser Val Pro Ala Met Ser Phe Gly Tyr
            195                 200                 205

Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Pro Met Leu Arg Ala Val Arg Ile Ile Ala Glu Glu
                245                 250                 255

Thr Thr Ala Met Leu Tyr Ser Cys Arg Thr Glu Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
        290

<210> SEQ ID NO 3
<211> LENGTH: 40
<212> TYPE: DNA
<213> ORGANISM: Homo sapiens

<400> SEQUENCE: 3
gtgattattt attatttatt tattatttat ttatttacag                    40

<210> SEQ ID NO 4
<211> LENGTH: 2913
<212> TYPE: DNA
<213> ORGANISM: Artificial Sequence
<220> FEATURE:
<223> OTHER INFORMATION: Insert sequence in pAx-ARETNF and pAx-ARETNF-R

<400> SEQUENCE: 4
tgacgtgtag tgtatttata cccggtgagt tcctcaagag gccactcttg agtgccagcg      60
agtagagttt tctcctccga gccgctccga caccgggact gaaaatgaga catattatct    120
gccacggagg tgttattacc gaagaaatgg ccgccagtct tttggaccag ctgatcgaag    180
aggtactggc tgataatctt ccacctccta gccattttga accacctacc cttcacgaac    240
tgtatgattt agacgtgacg gcccccgaag atcccaacga ggaggcggtt tcgcagattt    300
ttcccgactc tgtaatgttg gcggtgcagg aagggattga cttactcact tttccgccgg    360
cgcccggttc tccggagccg cctcaccttt cccggcagcc cgagcagccg gagcagagag    420
ccttgggtcc ggtttctatg ccaaaccttg taccggaggt gatcgatctt acctgccacg    480
aggctggctt tccacccagt gacgacgagg atgaagaggg tgaggagttt gtgttagatt    540
atgtggagca ccccgggcac ggttgcaggt cttgtcatta tcaccggagg aatacggggg    600
acccagatat tatgtgttcg ctttgctata tgaggacctg tggcatgttt gtctacagta    660
agtgaaaatt atgggcagtg ggtgatagag tggtgggttt ggtgtggtaa ttttttttttt    720 aattttaca gttttgtggt ttaaagaatt ttgtattgtg atttttttaa aaggtcctgt    780
gtctgaacct gagcctgagc ccgagccaga accgagcct gcaagaccta cccgccgtcc    840
taaaatggcg cctgctatcc tgagacgccc gacatcacct gtgtctagag aatgcaatag    900
tagtacggat agctgtgact ccggtccttc taacacacct cctgagatac acccggtggt    960
cccgctgtgc cccattaaac cagttgccgt gagagttggt gggcgtcgcc aggctgtgga   1020
```

```
atgtatcgag gacttgctta acgagcctgg gcaacctttg gacttgagct gtaaacgccc    1080
caggccataa ggtgtaaacc tgtgattgcg tgtgtggttg tgattattta ttatttattt    1140
attatttatt tatttacaga acgcctttgt ttgctgaatg agttgatgta agtttaataa    1200
agggtgagat aatgtttaac ttgcatggcg tgttaaatgg ggcggggctt aaagggtata    1260
taatgcgccg tgggctaatc ttggttacat ctgacctcat ggaggcttgg gagtgtttgg    1320
aagattttc tgctgtgcgt aacttgctgg aacagagctc taacagtacc tcttggtttt    1380
ggaggtttct gtggggctca tcccaggcaa agttagtctg cagaattaag gaggattaca    1440
agtgggaatt tgaagagctt ttgaaatcct gtggtgagct gtttgattct ttgaatctgg    1500
gtcaccaggc gcttttccaa gagaaggtca tcaagacttt ggattttcc acccggggc     1560
gcgctgcggc tgctgttgct ttttgagtt ttataaagga taaatggagc gaagaaaccc    1620
atctgagcgg ggggtacctg ctggattttc tggccatgca tctgtggaga gcggttgtga    1680
gacacaagaa tcgcctgcta ctgttgtctt ccgtccgccc ggcgataata ccgacggagg    1740
agcagcagca gcagcaggag gaagccaggc ggcggcggca ggagcagagc ccatggaacc    1800
cgagagccgg cctggaccct cgggaatgaa tgttgtacag gtggctgaac tgtatccaga    1860
actgagacg attttgacaa ttacagagga tgggcagggg ctaaaggggg taaagaggga    1920
gcgggggggct tgtgaggcta cagaggaggc taggaatcta gcttttagct taatgaccag    1980
acaccgtcct gagtgtatta cttttcaaca gatcaaggat aattgcgcta atgagcttga    2040
tctgctggcg cagaagtatt ccatagagca gctgaccact tactggctgc agccagggga    2100
tgattttgag gaggctatta gggtatatgc aaaggtggca cttaggccag attgcaagta    2160
caagatcagc aaacttgtaa atatcaggaa ttgttgctac atttctggga acggggccga    2220
ggtggagata gatacggagg ataggtggc ctttagatgt agcatgataa atatgtggcc    2280
gggggtgctt ggcatggacg gggtggttat tatgaatgta aggtttactg gccccaattt    2340
tagcggtacg gttttcctgg ccaataccaa ccttatccta cacggtgtaa gcttctatgg    2400
gtttaacaat acctgtgtgg aagcctggac cgatgtaagg gttcggggct gtgccttta    2460
ctgctgctgg aaggggtgg tgtgtcgccc caaaagcagg gcttcaatta agaaatgcct    2520
ctttgaaagg tgtaccttgg gtatcctgtc tgagggtaac tccagggtgc gccacaatgt    2580
ggcctccgac tgtggttgct tcatgctagt gaaaagcgtg gctgtgatta agcataacat    2640
ggtatgtggc aactgcgagg acagggcctc tcagatgctg acctgctcgg acggcaactg    2700
tcacctgctg aagaccattc acgtagccag ccactctcgc aaggcctggc cagtgtttga    2760
gcataacata ctgacccgct gttccttgca tttgggtaac aggagggggg tgttcctacc    2820
ttaccaatgc aatttgagtc acactaagat attgcttgag cccgagagca tgtccaaggt    2880
gaacctgaac ggggtgtttg acatgaccat gaa                                 2913
```

<210> SEQ ID NO 5
<211> LENGTH: 152
<212> TYPE: DNA
<213> ORGANISM: Adenovirus type 5

<400> SEQUENCE: 5

```
ggatgtggca aaagtgacgt ttttggtgtg cgccggtgta cacaggaagt gacaattttc     60
gcgcggtttt aggcggatgt tgtagtaaat ttgggcgtaa ccgagtaaga tttggccatt    120
ttcgcgggaa aactgaataa gaggaagtga aa                                  152
```

<210> SEQ ID NO 6
<211> LENGTH: 69
<212> TYPE: DNA
<213> ORGANISM: Homo sapiens

<400> SEQUENCE: 6
ttttattgtg tttttaattt atttattaag atggattctc agatatttat attttattt    60 tatttttt                                                             69

<210> SEQ ID NO 7
<211> LENGTH: 2942
<212> TYPE: DNA
<213> ORGANISM: Artificial Sequence
<220> FEATURE:
<223> OTHER INFORMATION: Insert sequence in pAx-AREFOS and pAx-AREFOS-R

<400> SEQUENCE: 7
tgacgtgtag tgtatttata cccggtgagt tcctcaagag gccactcttg agtgccagcg    60
agtagagttt tctcctccga gccgctccga caccgggact gaaaatgaga catattatct   120
gccacggagg tgttattacc gaagaaatgg ccgccagtct tttggaccag ctgatcgaag   180
aggtactggc tgataatctt ccacctccta gccattttga accacctacc cttcacgaac   240
tgtatgattt agacgtgacg gccccgaag atcccaacga ggaggcggtt tcgcagattt     300
ttcccgactc tgtaatgttg gcggtgcagg aagggattga cttactcact tttccgccgg   360
cgcccggttc tccggagccg cctcaccttt cccggcagcc cgagcagccg gagcagagag   420
ccttgggtcc ggtttctatg ccaaaccttg taccggaggt gatcgatctt acctgccacg   480
aggctggctt tccacccagt gacgacgagg atgaagaggg tgaggagttt gtgttagatt   540
atgtggagca ccccgggcac ggttgcaggt cttgtcatta tcaccggagg aatacggggg   600
acccagatat tatgtgttcg ctttgctata tgaggacctg tggcatgttt gtctacagta   660
agtgaaaatt atgggcagtg ggtgatagag tggtgggttt ggtgtggtaa tttttttttt   720 aattttttaca gttttgtggt ttaaagaatt ttgtattgtg attttttttaa aaggtcctgt  780 gtctgaacct gagcctgagc ccgagccaga accggagcct gcaagaccta cccgccgtcc   840
taaaatggcg cctgctatcc tgagacgccc gacatcacct gtgtctagag aatgcaatag   900
tagtacggat agctgtgact ccggtccttc taacacacct cctgagatac acccggtggt   960
cccgctgtgc cccattaaac cagttgccgt gagagttggg gggcgtcgcc aggctgtgga  1020
atgtatcgag gacttgctta acgagcctgg gcaacctttg gacttgagct gtaaacgccc  1080
caggccataa ggtgtaaacc tgtgattgcg tgtgtggtt tttattgtgt ttttaattta   1140
tttattaaga tggattctca gatatttata ttttatttt atttttttaa cgcctttgtt   1200
tgctgaatga gttgatgtaa gtttaataaa gggtgagata atgtttaact tgcatggcgt  1260
gttaaatggg gcgggggctta agggtatat aatgcgccgt gggctaatct tggttacatc   1320
tgacctcatg gaggcttggg agtgtttgga agattttttct gctgtgcgta acttgctgga  1380
acagagctct aacagtacct cttggttttg gaggtttctg tggggctcat cccaggcaaa  1440
gttagtctgc agaattaagg aggattacaa gtgggaattt gaagagcttt tgaaatcctg  1500
tggtgagctg tttgattctt tgaatctggg tcaccaggcg cttttccaag agaaggtcat  1560
caagactttg gattttttcca caccggggcg cgctgcggct gctgttgctt ttttgagttt  1620
tataaaggat aaatgagcg aagaaaccca tctgagcggg gggtacctgc tggattttct   1680
ggccatgcat ctgtggagag cggttgtgag acacaagaat cgcctgctac tgttgtcttc  1740

```
cgtccgcccg gcgataatac cgacggagga gcagcagcag cagcaggagg aagccaggcg    1800
gcggcggcag gagcagagcc catggaaccc gagagccggc ctggaccctc gggaatgaat    1860
gttgtacagg tggctgaact gtatccagaa ctgagacgca ttttgacaat tacagaggat    1920
gggcaggggc taaaggggt aaagagggag cgggggggctt gtgaggctac agaggaggct    1980
aggaatctag cttttagctt aatgaccaga caccgtcctg agtgtattac ttttcaacag    2040
atcaaggata attgcgctaa tgagcttgat ctgctggcgc agaagtattc catagagcag    2100
ctgaccactt actggctgca gccaggggat gattttgagg aggctattag ggtatatgca    2160
aaggtggcac ttaggccaga ttgcaagtac aagatcagca aacttgtaaa tatcaggaat    2220
tgttgctaca tttctgggaa cggggccgag gtggagatag atacggagga tagggtggcc    2280
tttagatgta gcatgataaa tatgtggccg ggggtgcttg gcatggacgg ggtggttatt    2340
atgaatgtaa ggtttactgg ccccaatttt agcggtacgg ttttcctggc caataccaac    2400
cttatcctac acggtgtaag cttctatggg tttaacaata cctgtgtgga agcctggacc    2460
gatgtaaggg ttcggggctg tgccttttac tgctgctgga aggggggtggt gtgtcgcccc    2520 aaaagcaggg cttcaattaa gaaatgcctc tttgaaaggt gtaccttggg tatcctgtct    2580
gagggtaact ccagggtgcg ccacaatgtg gcctccgact gtggttgctt catgctagtg    2640
aaaagcgtgg ctgtgattaa gcataacatg gtatgtggca actgcgagga cagggcctct    2700
cagatgctga cctgctcgga cggcaactgt cacctgctga agaccattca cgtagccagc    2760
cactctcgca aggcctggcc agtgtttgag cataacatac tgacccgctg ttccttgcat    2820
ttgggtaaca ggagggggt gttcctacct taccaatgca atttgagtca cactaagata    2880
ttgcttgagc ccgagagcat gtccaaggtg aacctgaacg gggtgtttga catgaccatg    2940
aa                                                                   2942
```

<210> SEQ ID NO 8
<211> LENGTH: 19
<212> TYPE: DNA
<213> ORGANISM: Artificial Sequence
<220> FEATURE:
<223> OTHER INFORMATION: synthesized oligonucleotide, E1A forward primer

<400> SEQUENCE: 8
gaaccaccta cccttcacg                                                  19

<210> SEQ ID NO 9
<211> LENGTH: 20
<212> TYPE: DNA
<213> ORGANISM: Artificial Sequence
<220> FEATURE:
<223> OTHER INFORMATION: synthesized oligonucleotide, E1A reverse primer

<400> SEQUENCE: 9
ccgccaacat tacagagtcg                                                 20

MODIFIED ADENOVIRUS AND MEDICINE COMPRISING SAME

CROSS-REFERENCE TO RELATED APPLICATIONS

This application is a U.S. national phase application of International Application No. PCT/JP2020/012196, filed Mar. 19, 2020, claiming the benefit of Japanese Application No. 2019-053895, filed Mar. 20, 2019, the contents of each of which are incorporated herein by their entireties for all purposes.

REFERENCE TO SEQUENCE LISTING

The present application is being filed along with a Sequence Listing in electronic format. The Sequence Listing is provided as a file entitled BCL-116US_Sequence Listing, created Sep. 14, 2021, which is 12.9 KB in size. The information in the electronic format of the Sequence Listing is identical to that in International Application No. PCT/JP2020/012196 and incorporated herein by reference in its entirety.

FIELD

The present invention relates to a modified adenovirus into which a gene encoding an AU-rich element is incorporated. The modified adenovirus has a specific cytocidal activity against a cell in which the stabilization of an mRNA containing an AU-rich element is enhanced. The present invention also relates to a medicine containing the modified adenovirus.

BACKGROUND

In the treatment of cancer, it is still an important issue to ensure both effectiveness in attacking cancer cells and safety not to attack normal cells or not to cause severe side effects on patients. To address this issue, cancer treatment using what is called an oncolytic virus, which exhibits a cancer cell-specific cytocidal effect, has been developed and put into practical use.

A typical oncolytic virus example is an adenovirus called Onyx-015, in which a gene encoding E1B55K is deleted (Non-patent Literature 1). This adenovirus cannot express a 55 kDa protein (E1B55K) encoded by E1B gene, and has a cytocidal effect on a tumor cell in which a tumor suppressor gene p53 does not normally function (including the case where a mutant p53 is expressed), or on a tumor cell in which the mRNA of a virus late gene is transported to the outside of a nucleus. However, it has been said that tumor cells in which the p53 does not normally function account for approximately 50% of all the cancer types, and the problem that the application of Onyx-015 is limited to these cancer types has been pointed out.

The inventor of the present invention has mainly aimed to extend an applicable range of tumors, paid attention to the fact that the stabilization of an mRNA containing an AU-Rich Element (also called an AU-rich sequence, hereinafter referred to as an ARE) was enhanced in a tumor cell, and developed a modified virus in which the ARE was introduced into the 3'-untranslated region of a viral gene essential for the replication of the virus itself or at a position adjacent to the 3'-untranslated region, and a modified adenovirus having a modified E4orf6 (Early region 4 open reading frame 6) gene (Patent Literature 1).

The ARE is a region rich in adenine (A) and uracil (U) present in an mRNA 3'-end untranslated region, and is high-frequently present in the 3'-untranslated region of the mRNA transcribed from a proliferation-related gene, such as an oncogene or a cytokine gene. It is known that an mRNA containing the ARE (hereinafter, referred to as an ARE-mRNA) is promptly degraded when Tristetraprolin (TTP), Zfp36L1, Zfp36L2, AUF1, KSRP, or the like recognizes the ARE and binds thereto. Meanwhile, HuR protein binds to the ARE, and in a cell having received various stresses, the ARE-mRNA is transported to the cytoplasm by HuR, and stabilized.

Since HuR is constitutively localized in cytoplasm in specific cells, such as tumor cells or inflammation-related cells, it is expected that when a modified virus with an ARE is infected the cells in which an ARE-mRNA is constitutively stabilized by HuR, the virus proliferates selectively in these cells. On the other hands, this virus is expected to exert its efficacy and safety because it does not proliferate in normal cells. One of the most important objects regarding oncolytic viruses is to ensure the effectiveness and safety, in particular, ensure safety.

CITATION LIST

Non Patent Literature

Non Patent Literature 1: Bischoff et al., Science, 1996, Vol. 274, pp. 373-376

Patent Literature

Patent Literature 1: Japanese Patent Application Laid-open No. 2016-160249

SUMMARY

Technical Problem

An object of the present invention is to provide a modified adenovirus having a cytocidal activity against a target cell and having a high degree of safety.

Solution to Problem

The inventor of the present invention has found that, in the modified adenovirus into which an ARE is introduced as described in in Patent Literature 1, the distance between an Early region 1A (E1A) gene and an enhancer sequence that enhances the expression of the E1A gene can be regulated, whereby safety can be enhanced while maintaining an oncolytic activity, and thus accomplished the following aspects according to the present invention.

(1) A modified adenovirus, containing: an E1A gene; an enhancer sequence having the function of increasing the expression of the E1A gene; and an AU-rich element introduced into the 3'-untranslated region of a viral gene essential for the proliferation of the virus itself or at a position adjacent to the 3'-untranslated region, wherein the distance between an E1A gene 5'-end and an enhancer sequence end is 1,500 bp to 4,500 bp.

(2) The modified adenovirus according to (1), wherein the viral gene essential for the proliferation of the virus itself is an E1A gene.

(3) A modified adenovirus, containing: an E1A gene: and an enhancer sequence having the function of increasing the expression of the E1A gene, the modified adenovirus being incapable of expressing a normal E4orf6 protein, wherein the distance between an E1A gene 5'-end and an enhancer sequence end is 1,500 bp to 4,500 bp.
(4) The modified adenovirus according to (3), being an adenovirus modified so as not to express an E4orf6 protein having an α-helix structure in an oncodomain.
(5) The modified adenovirus according to (4), containing a modified E4orf6 gene, the modified E4orf6 gene consisting of a nucleic acid sequence of SEQ ID NO: 1 or a nucleic acid sequence encoding an amino acid sequence identical to an amino acid sequence encoded by the nucleic acid sequence of SEQ ID NO: 1.
(6) The modified adenovirus according to (4), containing a modified E4orf6 gene encoding an amino acid sequence of SEQ ID NO: 2.
(7) The modified adenovirus according to (4), being an adenovirus in which the E4orf6 is deleted.
(8) The modified adenovirus according to any one of (3) to (7), containing an ARE introduced into the 3'-untranslated region of a viral gene essential for the proliferation of the virus itself or at a position adjacent to the 3'-untranslated region.
(9) The modified adenovirus according to (8), wherein the viral gene essential for the proliferation of the virus itself is an E1A gene.
(10) A medicine for the treatment of a disease involving a cell in which the stabilization of an mRNA containing an AU-rich element is enhanced, the medicine containing the modified adenovirus according to any one of (1) to (9).
(11) The medicine according to (10), wherein the disease involving the cell in which the stabilization of the mRNA containing the AU-rich element is enhanced is a malignant tumor or rheumatism.

Advantageous Effects of Invention

According to the present invention, a modified adenovirus having a cytocidal activity against a target cell and having a high degree of safety can be provided, and a medicine containing the modified adenovirus can be a therapeutic agent effective not only to cancer, but also to rheumatism.

DESCRIPTION OF EMBODIMENTS

Figure 1:
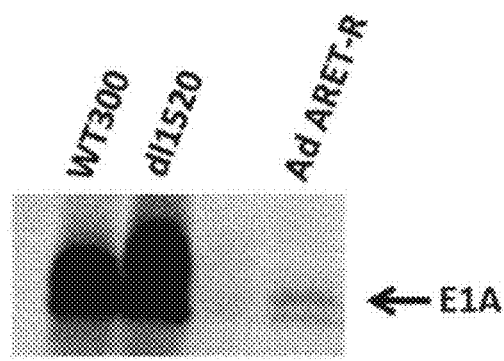
FIG. 1 is a diagram illustrating the result of Western blotting analysis of the expression level of E1A protein in A549 cells derived from human alveolar basal epithelial adenocarcinoma infected with modified adenovirus AdARET-R, wild type adenovirus wt300, or E1B55k-deficient adenovirus dl1520.

A first aspect of the present invention relates to a modified adenovirus containing: an E1A gene; an enhancer sequence having the function of increasing the expression of the E1A gene; and an ARE introduced into the 3'-untranslated region of a viral gene essential for the proliferation of the virus itself or at a position adjacent to the 3'-untranslated region, wherein the distance between an E1A gene 5'-end and an enhancer sequence end is 1,500 bp to 4,500 bp.

The modified adenovirus according to the present invention contains an E1A gene and an enhancer sequence having the function of increasing the expression of the E1A gene.

There are 51 serotypes of adenoviruses. Although any serotype of adenovirus can be used in the present invention, a type 5 adenovirus, which is often used as a viral vector, is preferably used.

The E1A gene is a gene the expression of which is induced first among adenovirus genes and that encodes an E1A protein activating the transcription of the adenovirus genes. The E1A protein has the function of inducing the expression of adenovirus early genes, namely, E4, E1B, E3, and E2 genes, and all adenovirus late genes.

The enhancer sequence (hereinafter, also simply referred to as an enhancer) is a nucleic acid sequence having the function of increasing gene expression in cooperation with a promoter that controls gene expression in eukaryotic DNA. In the present invention, the enhancer is not limited as long as the enhancer has the function of increasing the expression of the E1A gene, and the enhancer may be a unique enhancer present upstream of the E1A gene of adenovirus (E1A enhancer), or may be a heterologous enhancer incorporated to function in mammalian cells, such as a cytomegalovirus (CMV)-derived enhancer or a herpesvirus-derived enhancer. In the present invention, a particularly preferred enhancer is an E1A enhancer (SEQ ID NO: 5) located at −192 bp to −343 bp upstream of the E1A gene in type 5 adenovirus genomic DNA.

In the modified adenovirus according to the present invention, as long as the enhancer is arranged so as to be capable of increasing the expression of the E1A gene, the enhancer may be arranged upstream or downstream of the E1A gene, and furthermore, the direction of the enhancer nucleic acid sequence may be the same as or reverse to the transcription direction of the E1A gene. The lower limit of the distance between the E1A gene 5'-end and the enhancer sequence end is 1,500 bp, preferably 2,500 bp, and more preferably 2,900 bp, and the upper limit thereof is 4,500 bp, preferably 3,500 bp, and more preferably 3,200 bp. The distance between the E1A gene 5'-end and the enhancer sequence end is, for example, 1,500 bp to 4,500 bp, 2,500 bp to 3,500 bp, or 2,900 bp to 3,200 bp. Here, the distance between the E1A gene 5'-end and the enhancer sequence end means the number of bases present between the base of the E1A gene 5'-end and the base of an enhancer sequence end closer to the E1A gene, irrespective of the arrangement and direction of the E1A gene and the enhancer. A nucleic acid sequence between the E1A gene 5'-end and the enhancer sequence end is not particularly limited, and other genes may be present therein, or, for example, an untranscribed sequence or an untranslated sequence may be present therein.

The modified adenovirus of the first aspect contains an ARE introduced into the 3'-untranslated region of a viral gene essential for the proliferation of the virus itself or at a position adjacent to the 3'-untranslated region.

The ARE beneficially has the function of controlling the stability of an ARE-mRNA in a cell, in relation to a protein that promotes the degradation of the ARE-mRNA, such as Tristetraprolin (TTP), Zfp36L1, Zfp36L2, AUF1, or KSRP, or a protein that stabilizes an ARE-mRNA, such as HuR. It is known that the ARE is present in the 3'-untranslated regions of various genes involved in proliferation, differentiation induction, or immune responses of animal cells, such as a c-fos gene, a c-myc gene, a TNF-α gene, and a cox-2 gene, and many types of nucleic acid sequences have been reported. In the present invention, any of such AREs can be used, and an ARE present in human genes is particularly preferably used. The number of AREs introduced may be one or two or more, and the number of types of AREs introduced may be one or two or more. In the present invention, preferred examples of the ARE include an ARE (SEQ ID NO: 3) contained in a human TNF-α gene and an ARE (SEQ ID NO: 6) contained in a human c-fos gene.

The ARE in the present invention includes not only a nucleic acid sequence rich in A and U in an RNA molecule, but also a nucleic acid sequence rich in A and T (thymine) corresponding to an ARE in a DNA molecule. Therefore, the expression "containing an ARE" or "an ARE is contained" is used not only when the ARE is contained in an RNA molecule, but also when a nucleic acid sequence rich in A and T that corresponds to the ARE in a DNA molecule is contained. The expression "an ARE is introduced" means that a nucleic acid sequence, rich in A and T, corresponding to the ARE is incorporated into a genome or a DNA molecule encoding a gene so as to include the ARE in an mRNA molecule that is the transcript of the genome or the DNA molecule.

Examples of the viral gene essential for the proliferation of the virus itself, into which the ARE is introduced, include an E1A gene, an E1B gene, an E4orf6 gene, and an E4orf3 gene, and an E1A gene is preferably used. In the case where an E1A gene is used as the viral gene into which the ARE is introduced, the modified adenovirus of the first aspect is a modified adenovirus containing: an E1A gene containing the ARE introduced into the 3'-untranslated region or at a position adjacent to the 3'-untranslated region; and an enhancer sequence having the function of increasing the expression of the E1A gene, wherein the distance between an E1A gene 5'-end and an enhancer sequence end is 1,500 bp to 4,500 bp.

The ARE is introduced into the 3'-untranslated region or at a position adjacent to the 3'-untranslated region of the viral gene. The ARE is particularly preferably introduced at a position behind a stop codon of an ORF of the viral gene and before the starting point of a poly A sequence. The position adjacent to the 3'-untranslated region of the viral gene means a position that enables an mRNA transcribed from the viral gene by an RNA polymerase to include the ARE at its 3'-end by the read-through of the RNA polymerase.

As described above, the ARE has the function of promoting the prompt degradation of an mRNA containing the ARE in association with TTP or other proteins. Thus, by introducing the ARE into the 3'-untranslated region of the viral gene essential for the proliferation of the virus itself or at a position adjacent to the 3'-untranslated region, an mRNA transcribed from the viral gene can be made instable. Without being bound by the following inference, the modified virus of the first aspect of the present invention cannot proliferate in a normal cell in which an ARE-mRNA is promptly degraded because a protein essential to proliferation that is encoded by the ARE-mRNA is not expressed therein, whereas the modified virus of the first aspect can proliferate in a cell in which the stabilization of an ARE-mRNA is enhanced because the protein essential to proliferation is stably expressed therein.

The modified adenovirus of the first aspect can be produced using various genetic engineering methods known to those skilled in the art. For example, a nucleic acid fragment containing: a viral gene, essential for the proliferation of the virus itself, into the 3'-untranslated region of which or at a position adjacent to the 3'-untranslated region of which an ARE is introduced; and an E1A gene is incorporated into a cosmid vector pAxcwit or pAxcwit2 containing an adenovirus genomic DNA containing an enhancer having the function of increasing the expression of the E1A gene so that the distance between an E1A gene 5'-end and an enhancer sequence end is 1,500 bp to 4,500 bp, whereby a modified adenovirus DNA can be constructed. In the case where an E1A gene is used as a viral gene essential for the proliferation of the virus itself, a nucleic acid fragment containing the E1A gene into the 3'-untranslated region of which or at a position adjacent to the 3'-untranslated region of which an ARE is introduced is incorporated into a cosmid vector pAxcwit or pAxcwit2 containing an adenovirus genomic DNA containing an enhancer having the function of increasing the expression of the E1A gene so that the distance between an E1A gene 5'-end and an enhancer sequence end is 1,500 bp to 4,500 bp, whereby a modified adenovirus DNA can be constructed.

In the case where an adenovirus DNA having no enhancer is used as a basis, for example, a nucleic acid fragment containing: a viral gene, essential for the proliferation of the virus itself, into the 3'-untranslated region of which or at a position adjacent to the 3'-untranslated region of which an ARE is introduced; an E1A gene; and an enhancer, wherein the distance between an E1A gene 5'-end and an enhancer sequence end is 1,500 bp to 4,500 bp, is incorporated into the adenovirus DNA, whereby a modified adenovirus DNA can be constructed. In the case where an adenovirus DNA having no enhancer is used as a basis and where an E1A gene is used as a viral gene essential for the proliferation of the virus itself, a nucleic acid fragment containing: the E1A gene into the 3'-untranslated region of which or at a position adjacent to the 3'-untranslated region of which an ARE is introduced; and an enhancer, wherein the distance between an E1A gene 5'-end and an enhancer sequence end is 1,500 bp to 4,500 bp, is incorporated into the adenovirus DNA, whereby a modified adenovirus DNA can be constructed.

Subsequently, the constructed modified adenovirus DNA is transfected into a packaging cell, such as a HEK293 cell or a HEK293T cell, whereby, through the translation of a structural viral protein and the packaging of a viral genome, the modified adenovirus of the first aspect can be collected in the form of virus particles.

As long as the modified adenovirus of the first aspect contains the E1A gene, the enhancer, and the ARE introduced into the 3'-untranslated region of the viral gene essential for the proliferation of the virus itself or at a position adjacent to the 3'-untranslated region, and as long as the modified adenovirus is capable of proliferating in a target cell, the modified adenovirus may further contain other genes or may be deficient in a gene not essential to virus proliferation. For example, the above-mentioned cosmid vectors pAxcwit and pAxcwit2 are deficient in an E1A gene, an E1B gene, and an E3 gene, which are contained in wild type adenoviruses. In the case where the modified adenovirus according to the present invention is constructed using pAxcwit or pAxcwit2, an E1A gene needs to be incorporated. In contrast, an E1B gene and an E3 gene are less important for virus proliferation in a cell in which the stabilization of an ARE-mRNA is enhanced, than the E1A, and therefore, the modified adenovirus does not need to contain E1B and E3 genes.

Furthermore, as long as the modified adenovirus of the first aspect contains the E1A gene, the enhancer, and the ARE introduced into the 3'-untranslated region of the viral gene essential for the proliferation of the virus itself or at a position adjacent to the 3'-untranslated region, and as long as the modified adenovirus is capable of proliferating in a target cell, the position and direction of a gene in a genome of the modified adenovirus may be different from those in a wild type adenovirus.

Preferred examples of the modified adenovirus of the first aspect include a modified adenovirus in which an E1A TATA box; an E1A coding region; an E1B promoter; and a nucleic acid fragment including a partial sequence in an E1B coding region, specifically, a nucleic acid fragment consisting of a nucleic acid sequence from an E1B mRNA starting point down to approximately 1,627 bp downstream are incorporated in this order in a direction reverse to the direction of the nucleic acid sequence of an E1A enhancer, immediately below the nucleic acid sequence of the E1A enhancer, and furthermore, an ARE is incorporated into the 3'-untranslated region of an E1A gene.

The enhancement of the cytocidal activity of the modified adenovirus according to the present invention against tumor cells is inferred as follows. When the modified adenovirus infects a tumor cell, an E1A-ARE mRNA is transcribed in suitable amounts by the moderate transcription enhancement effect of the enhancer. The transcribed E1A-ARE mRNA is transported to the cytoplasm in the tumor cell, and an E1A protein is stably synthesized, and the adenovirus proliferates, so that the tumor cell is lysed. Another preferred example of the modified adenovirus according to the present invention does not have a complete E1B gene, and therefore, it is thought that the modified adenovirus may additionally have a property equivalent to that of the above-mentioned Onyx-015.

Another aspect of the present invention relates to a modified adenovirus containing an E1A gene and an enhancer sequence having the function of increasing the expression of the E1A gene, and being incapable of expressing a normal E4orf6 protein, wherein the distance between an E1A gene 5'-end and an enhancer sequence end is 1,500 bp to 4,500 bp.

The E4orf6 protein is a gene product of E4orf6, which is one of adenovirus early genes. It is known that the E4orf6 protein interacts with a pp32 protein in an oncodomain on the C-terminus side of the E4orf6 protein (in the case of a type 5 adenovirus, the oncodomain corresponds to positions 204 to 294 in the amino acid sequence of E4orf6); an α-helix structure present in the oncodomain is involved in the above-mentioned interaction; and, through this interaction, the E4orf6 protein and the pp32 bind to an mRNA containing an ARE in its 3'-untranslated region via a HuR protein directly binding to the ARE, so that the mRNA containing the ARE is forcibly and constantly transported to the cytoplasm and stabilized independently of CRM1 (Higashino et al, J. Cell Biol., 2005, Vol. 170, pp. 15-20). In the present invention, "being incapable of expressing a normal E4orf6 protein" means being incapable of expressing an E4orf6 protein having a function equivalent to that of a wild type E4orf6 protein, and typically means being incapable of expressing an E4orf6 protein in which the α-helix structure in the oncodomain is retained due to deletion of all or a part of the nucleic acid sequence encoding the oncodomain of the E4orf6 protein, or due to one or more mutations in the nucleic acid sequence.

The preferred modified adenovirus of the above-mentioned aspect is a modified adenovirus that contains an E1A gene and an enhancer sequence having the function of increasing the expression of the E1A gene, and contains a modified E4orf6 gene consisting of a nucleic acid sequence of SEQ ID NO: 1 or a nucleic acid sequence encoding the same amino acid sequence as an amino acid sequence encoded by the nucleic acid sequence of SEQ ID NO: 1; a modified adenovirus that contains an E1A gene and an enhancer sequence having the function of increasing the expression of the E1A gene, and contains a modified E4orf6 gene encoding an amino acid sequence of SEQ ID NO: 2; or a modified adenovirus that contains an E1A gene and an enhancer sequence having the function of increasing the expression of the E1A gene and is deficient in an E4orf6, wherein the distance between an E1A gene 5'-end and an enhancer sequence end is 1,500 bp to 4,500 bp.

Examples of the modified adenovirus having a modified E4orf6 gene consisting of a nucleic acid sequence of SEQ ID NO: 1 include an adenovirus, referred to as dl355, described in Halbert et al, J. Virology, 1985, Vol. 56, 250-257. Examples of the adenovirus in which an E4orf6 is deleted include an adenovirus, referred to as dl366, described in the above-mentioned literature by Halbert et al. The modified adenovirus according to the present invention can be produced, based on dl355 or dl366, by recombination so as to achieve a distance between an E1A gene 5'-end and an enhancer sequence end of 1,500 bp to 4,500 bp. Here, the enhancer, the distance between the E1A gene and the enhancer, and a positional relation between the E1A gene and the enhancer are as those described in the first aspect. A modified adenovirus containing a modified E4orf6 gene consisting of a nucleic acid sequence that encodes an amino acid sequence encoded by the nucleic acid sequence of SEQ ID NO: 1, even though the modified E4orf6 gene consists of a different nucleic acid sequence from the nucleic acid sequence of SEQ ID NO: 1, due to so-called codon condensation, also constitutes one aspect of the present invention.

The modified adenovirus according to the present invention can exhibit high proliferation potency and cytocidal activity in a cell in which the stabilization of an ARE-mRNA is enhanced, and therefore, the modified adenovirus can be utilized as a medicine for the treatment of a disease involving such cell. Thus, as another aspect, the present invention provides a medicine containing the adenovirus for the treatment of a disease involving a cell in which the stabilization of an ARE-mRNA is enhanced, containing the above-mentioned modified virus.

In the present invention, the expression "the stabilization of an ARE-mRNA is enhanced" means not a condition in which an ARE-mRNA is temporarily stabilized by various stresses, but a condition in which, without the above-mentioned stresses, an ARE-mRNA can be constantly stabilized in a cell, as can be seen in a tumor cell.

One example of a host cell in which the stabilization of ARE-mRNA is enhanced is a tumor cell (Lopez et al, Oncogene, 2003, 22: 7146-7154). Therefore, the medicine containing the modified adenovirus according to the present invention can be used as an anti-tumor drug.

Other examples of the host cell in which the stabilization of an ARE-mRNA is enhanced are a peripheral mononuclear cell and a synovial cell in rheumatism patients (Thiele, et al., Exp. Cell Res., 2006, Vol. 312. No. 12). It is known that, in a peripheral mononuclear cell in rheumatism patients, than in a peripheral mononuclear cell healthy subjects, the expression of TTP, which promotes the degradation of an ARE-mRNA, is greatly reduced while the expression of TNF-α translated from an ARE-mRNA is abnormally enhanced, from which the enhanced stabilization of the ARE-mRNA is inferred. Therefore, infection of a peripheral mononuclear cell and a synovial cell with the modified adenovirus according to the present invention is expected to selectively kill the peripheral mononuclear cell, suppress the expression of TNF-α and the induction of osteoclasts due to inflammation, and further suppress the proliferation of the synovial cell, which is the target for inflammation, thereby suppressing the progression or aggravation of rheumatism. Thus, the medicine containing the modified adenovirus according to the present invention can be used as a medicine for the treatment of rheumatism.

The term "treatment" used herein includes every type of medically acceptable therapeutic intervention intended for cure or transient remission of a disease. That is, the treatment of a disease involving a cell in which the stabilization of an mRNA containing an ARE is enhanced includes medically acceptable intervention intended for various purposes, including a delay or arrest in the progression of the disease, and regression or disappearance of a lesion in the disease.

The present invention provides a medicine containing the modified adenovirus of each of the above-mentioned aspects. The medicine may be in the form of a pharmaceutical composition including not only the modified adenovirus, but also any other viruses, a therapeutically effective agent, a pharmaceutically acceptable carrier, a buffer, an excipient, an adjuvant, an antiseptic, a filling agent, a stabilizing agent, a thickening agent, and/or any ingredient commonly used in pharmaceutical preparations.

Pharmaceutically acceptable ingredients are well known to those skilled in the art, and can be appropriately selected from, for example, ingredients described in the Japanese Pharmacopoeia, 17th Edition or other written standards, and used by those skilled in the art within the scope of their ordinary implementation ability, depending on dosage forms. Furthermore, various ingredients used in virus-containing pharmaceutical preparations are preferably used.

The medicine according to the present invention may be in any form suitable for administration, such as a solid, semisolid, or liquid form, such as a solution, freeze dry powder, an emulsion, a suspension, a tablet, a pellet, and a capsule, but not limited to these forms. In a specific embodiment, the medicine is used in the form of a parenteral formulation such as an injection or a drip. Examples of the carrier that can be used in the parenteral formulations include aqueous carriers commonly used in pharmaceutical preparations, such as physiological saline and an isotonic solution containing glucose, D-sorbitol, or the like.

The medicine in the above-mentioned form can be produced by, for example, a conventional method for producing a medicine containing an oncolytic virus and other viral vectors described in Non Patent Literature 1 (Bischoff et al., Science, 1996, Vol. 274, pp. 373-376) or a method modified with ordinary abilities of those skilled in the art.

The medicine according to the present invention is administered to a subject, including a companion animal, such as a dog and cat, a livestock animal, such as a cow and pig, and a primate, such as a human, and in particular, the medicine is administered to a human. Administration of the medicine to a subject can be performed in a manner similar to that for a conventional medicine containing an oncolytic virus and other viral vectors, for example described in Non Patent Literature 1. A route of the administration is determined by those skilled in the art in consideration of various factors that are taken into consideration on drug administration, such as the form of a pharmaceutical preparation, a disease, and a disease site.

Preferred examples of the route of the administration of the medicine according to the present invention include parenteral administration, such as intravascular administration (preferably, intravenous administration), intraperitoneal administration, intestinal administration, or local administration into a tumor or to the vicinity of a tumor. In one preferred embodiment, the medicine according to the present invention is administered to a subject by intravenous administration, or local administration into a tumor or to the vicinity of a tumor. The administration may be single-dose administration or repeated-dose administration.

The medicine according to the present invention is administered in effective amounts for the treatment of a disease, the amounts being suitably determined depending on usage, the age of a subject, a disease condition, and other conditions. When the medicine according to the present invention is administered to a subject, particularly a human, the dosage can be in a range of, for example, $1\times10^3$ to $1\times10^{14}$, preferably $1\times10^5$ to $1\times10^{12}$, more preferably $1\times10^6$ to $1\times10^{11}$, and the most preferably $1\times10^7$ to $1\times10^{10}$ plaque formation units (p.f.u.) per human, and the above-mentioned dose of the medicine is administered once per day or divided into a plurality of fractions to be administered per day, or intermittently administered.

As another aspect, the present invention provides a method for treating a disease involving a cell in which the stabilization of an ARE-mRNA is enhanced, the method including administering an effective dose of the modified adenovirus of each of the above-mentioned aspects to a subject in need thereof.

While the medicine according to the present invention can be used alone to effectively treat the disease, the medicine may also be used in combination with any other treatments. For example, a conventional treatment and a treatment using the medicine according to the present invention may be combined. For example, in the case of a cancer therapy, the treatment using the medicine according to the present invention may be used in combination with chemotherapy using other anticancer drugs, cancer immunotherapy, or radiotherapy.

Hereinafter, the present invention will be described in more detail by way of non-limiting examples. In the examples, an operation using a commercial kit was performed in accordance with a kit manufacturer's protocol. It will be easily understood by those skilled in the art that the present invention is not limited to specific methodologies, protocols, cell strains, animal species or genus, constructs, and reagents described herein, and these can be appropriately changed.

EXAMPLES

Example 1

1) Preparation of Modified Adenovirus in which ARE is Introduced into 3'-Untranslated Region of E1A Gene pXhoIC (Logan et al, Cancer Cells 2, 527-532, 1984), that is, a plasmid in which an E1 region containing the E1A gene and E1B gene of a type 5 adenovirus was inserted into the *Escherichia coli* plasmid vector pBR322 provided by Dr. T. Shenk of Princeton University, was ring-opened with the restriction enzyme HpaI. Into the ring-opened plasmid, a synthesized double stranded DNA fragment consisting of: a nucleic acid sequence corresponding to the ARE (5'-gtgattattt attatttatt tattatttat ttatttacag-3', SEQ ID NO: 3) contained in the human TNF-α gene; and its complementary strand sequence was incorporated to construct pXhoIC-ARETNF, that is, a plasmid containing an E1 region in which the ARE was introduced into the 3'-untranslated region of the E1A gene.

Using the pXhoIC-ARETNF as a template, a PCR using a primer set containing 15 base pairs of the cosmid sequence at both ends was performed to prepare an amplified fragment of the E1 region into which the ARE was introduced. This amplified fragment was incorporated into the Smi I restriction site of pAxcwit2 (Takara Bio Inc.), which contains an adenovirus genome deficient in the E1A gene and E1B gene, by the In-Fusion (registered trademark) method to construct pAx-ARETNF and pAx-ARETNF-R as plasmids containing the adenovirus genome in which the ARE was introduced into the 3'-untranslated region of the E1A gene.

The nucleic acid sequence of the insert contained in both of the plasmids is represented by SEQ ID NO: 4. pAx-ARETNF contains this insert in the same direction as that of the E1A enhancer contained in pAxcwit2, whereas pAx-ARETNF-R contains this insert in the reverse direction to that of the E1A enhancer contained in pAxcwit2. In the nucleic acid sequence of SEQ ID NO: 4, bases at positions 1 to 1217 correspond to the E1A gene, in which bases at positions 1 to 43 correspond to the E1A upstream region containing TATA box, bases at positions 105 to 1090 (partially containing intron) correspond to the E1A coding region, and bases at positions 1091 to 1217 correspond to the 3'-untranslated region of the E1A gene, wherein bases at positions 1120 to 1159 correspond to the introduced ARE derived from the human TNF-α gene. Furthermore, bases at positions 1218 to 2913 correspond to a part of the E1B gene (up to the middle of the E1B55k coding region in the E1B gene). Furthermore, the distance between the E1A mRNA starting point and the enhancer sequence end in pAx-ARETNF is 203 bp, whereas the distance between the E1A mRNA starting point and the enhancer sequence end in pAx-ARETNF-R is 3,029 bp.

Using Hilymax (DOJINDO LABORATORIES), 293 cells were infected with stranded DNA obtained by cleaving each of pAx-ARETNF and pAx-ARETNF-R with the restriction enzyme pad to prepare a stock of the recombinant adenovirus. Furthermore, a purified virus ($9.0 \times 10^9$ virus-particles/mL) was prepared using Fast-Trap adenovirus purification kit (EMD Millipore). Hereinafter, these viruses are referred to as AdARET and AdARET-R, respectively.

Furthermore, 293 cells were infected with a wild type 5 adenovirus, namely wt300, (obtained from Dr. T Shenk) and a type 5 adenovirus deficient in E1B55k, namely dl1520, (provided by Dr. A. Berk of University of California) in the same manner as that described above to prepare purified viruses.

2) Evaluation of E1A Expression Level in Modified Virus $1 \times 10^5$ cells of human alveolar basal epithelial adenocarcinoma cell line A549 (purchased from ATCC) were inoculated into a 6-well-dish each well of which contained 2-ml DMEM (10%-FBS), and cultured at 37° C. The culture medium was removed, and 2 ml of DMEM containing 10%-FBS was newly added. Furthermore, AdARET-R prepared in the above-described 1) was added so as to achieve MOI=1000, or wt300 or dl1520 was added so as to achieve MOI=10. Incubation was performed at 37° C. for 24 hours for wt300 and dl1520, and for 48 hours for AdARET-R. Viruses were collected from the culture media, proteins were extracted, and then, E1A was detected by the Western blotting method using an M58 antibody. As a result, it was confirmed that the E1A expression level of AdARET-R was lower, compared with those of other viruses (FIG. 1).

Figure 2:
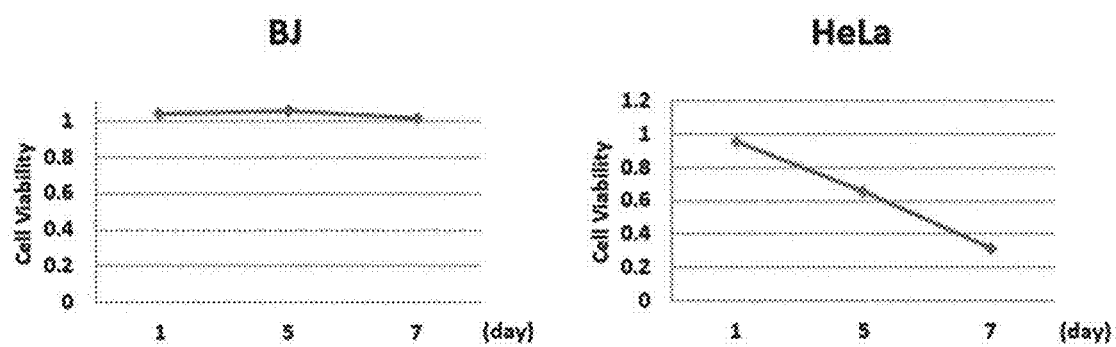
FIG. 2 is graphs each illustrating the cytocidal activity of modified adenovirus AdARET-R against BJ cells serving as normal cells, or HeLa cells derived from human cervical cancer.

3) Evaluation of Cytocidal Activity $3 \times 10^3$ foreskin dermal fibroblast-derived BJ cells serving as normal cells and $3 \times 10^3$ human cervical cancer-derived HeLa cells were each inoculated into a 96-well-dish each well of which contained 100 µl of DMEM (10%-FBS), and cultured at 37° C. The culture medium was removed, and 100 µl of DMEM containing 10%-FBS was newly added. Furthermore, AdARET-R prepared in the above-described 1) was added so as to achieve MOI=10,000, and incubation was performed at 37° C. One, five, and seven days after the start of culture, cell viability was measured by XTT assay using Cell Proliferation kit II (XTT) (Roche). Instead of addition of adenovirus, wells to which the culture medium having the same volume as that of the adenovirus was added were used as controls (mock), and the relative cell viability to the mock was calculated. As a result, it was confirmed that AdARET-R exhibited cytocidal activity against HeLa cells, whereas AdARET-R scarcely exhibited cytocidal activity against BJ cells serving as normal cells (FIG. 2).

4) Evaluation of Cytocidal Activity

Figure 3:
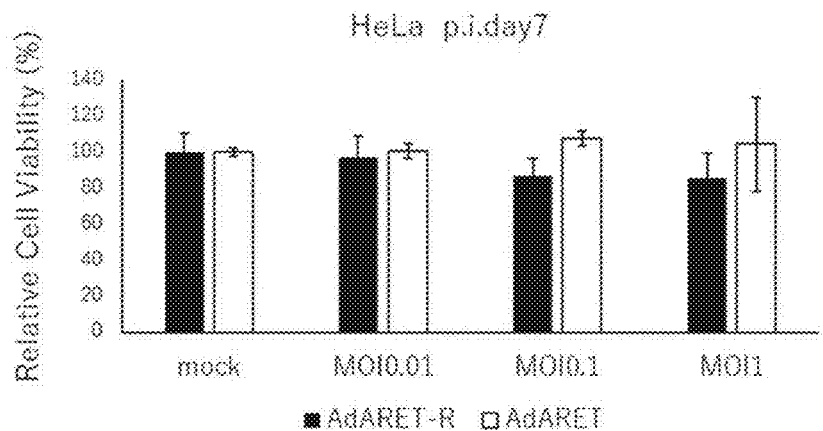
FIG. 3 is graphs illustrating the cytocidal activity of modified adenovirus AdARET-R against HeLa or A549 cells, in comparison with that of control adenovirus AdARET.
Figure 3:
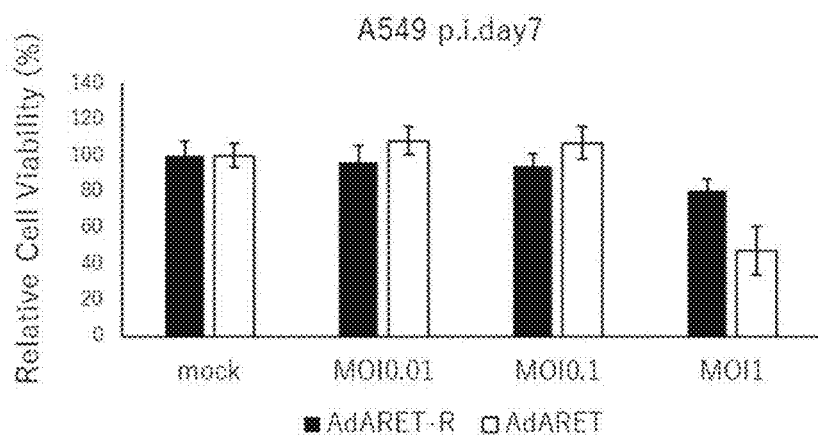

In the same manner as that in the above-described 3), AdARET-R or AdARET was added to HeLa cells and A549 cells so as to achieve MOI=0.01, 0.1, or 1, and incubation was performed. Seven days after the start of culture, cell viability was measured by XTT assay. As a result, it was confirmed that both AdARET-R and AdARET exhibited cytocidal activity against cancer cells, and AdARET-R exhibited stronger cytocidal activity against HeLa cells than AdARET, whereas AdARET exhibited stronger cytocidal activity against A549 cells than AdARET-R (FIG. 3).

5) Comparison of Cytocidal Activity Against Normal Cell

Figure 4:
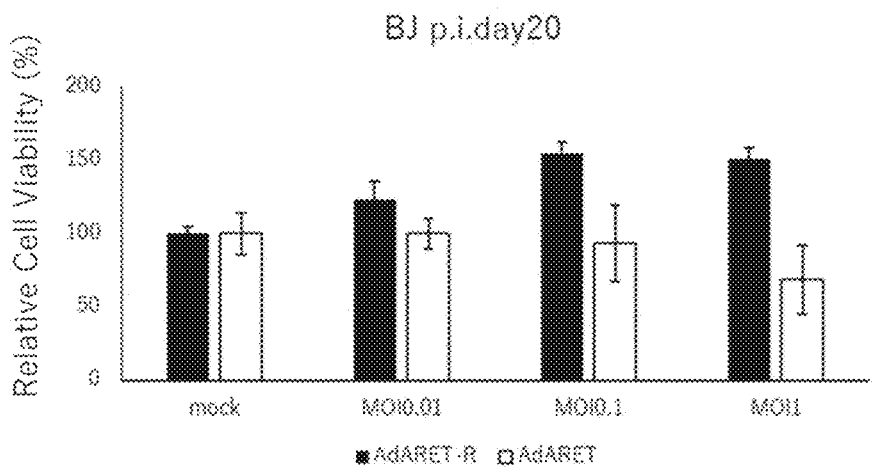
FIG. 4 is a graph illustrating the cytocidal activity of modified adenovirus AdARET-R against BJ cells, in comparison with that of control adenovirus AdARET.

In the same manner as that in the above-described 3), AdARET-R or AdARET was added to BJ cells so as to achieve MOI=0.01, 0.1, or 1, and incubation was performed. Twenty days after the start of culture, cell viability was measured by XTT assay. As a result, the cells infected with AdARET-R exhibited higher viability than the cells infected with AdARET (FIG. 4), it was confirmed that AdARET-R exhibited weaker cytocidal activity against normal cells than AdARET.

Example 2

1) Preparation of Modified Adenovirus in which c-Fos-Derived ARE is Introduced into 3'-Untranslated Region of E1A Gene pXhoIC was ring-opened with the restriction enzyme HpaI, and a synthesized double stranded DNA fragment consisting of: a nucleic acid sequence corresponding to the ARE (5'-tttt attgtgtttt taatttattt attaagatgg attctcagat atttatattt ttattttatt ttttt-3', SEQ ID NO: 6) contained in the human c-fos gene; and its complementary strand sequence was incorporated to construct pXhoIC-AREFOS, that is, a plasmid containing an E1 region in which the ARE was introduced into the 3'-untranslated region of the E1A gene.

Using the pXhoIC-AREFOS as a template, a PCR using a primer set containing 15 base pairs of the cosmid sequence at both ends was performed to prepare an amplified fragment of the E1 region into which the ARE was introduced. This amplified fragment was incorporated into the Smi I restriction site of pAxcwit2 by the In-Fusion (registered trademark) method to construct pAx-AREFOS and pAx-AREFOS-R as plasmids containing an adenovirus genome in which the ARE was introduced into the 3'-untranslated region of the E1A gene.

The nucleic acid sequence of the insert contained in both of the plasmids is represented by SEQ ID NO: 7. pAx-AREFOS contains this insert in the same direction as that of the E1A enhancer contained in pAxcwit2, whereas pAx-AREFOS-R contains this insert in the reverse direction to that of the E1A enhancer contained in pAxcwit2. In the nucleic acid sequence of SEQ ID NO: 7, bases at positions 1 to 1246 correspond to the E1A gene, in which bases at positions 1 to 43 correspond to the E1A upstream region containing TATA box, bases at positions 105 to 1090 (partially containing intron) correspond to the E1A coding region, and bases at positions 1091 to 1246 correspond to the 3'-untranslated region of the E1A gene, wherein bases at positions 1120 to 1188 correspond to the introduced ARE derived from the human c-fos gene. Furthermore, bases at positions 1247 to 2942 correspond to a part of the E1B gene (up to the middle of the E1B55k coding region in the E1B gene). Furthermore, the distance between the E1A mRNA starting point and the enhancer sequence end in pAx-AREFOS is 203 bp, whereas the distance between the E1A mRNA starting point and the enhancer sequence end in pAx-AREFOS-R is 3,058 bp.

Using Hilymax, 293 cells were infected with stranded DNA obtained by cleaving each of pAx-AREFOS and pAx-AREFOS-R with the restriction enzyme pad to prepare a stock of the recombinant adenovirus. Furthermore, a purified virus was prepared using Fast-Trap adenovirus purification kit. Hereinafter, these viruses are referred to as AdAREF and AdAREF-R, respectively.

Figure 5:
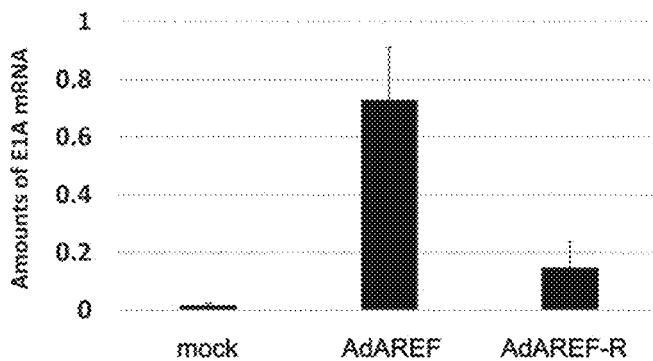
FIG. 5 is a graph illustrating the E1A expression level of modified adenovirus AdARET-R in A549 cells, in comparison with that of control adenovirus AdAREF.

2) Evaluation of E1A Expression Level in Modified Virus $1 \times 10^5$ cells of A549 cell line were inoculated into a 6-well-dish each well of which contained 2-ml DMEM (10%-FBS) and cultured at 37° C. The culture medium was removed, and 2 ml of DMEM containing 10%-FBS was newly added. Furthermore, AdAREF or AdAREF-R prepared in the above-described 1) was added so as to achieve MOI=10, and incubation was performed at 37° C. for 72 hours. mRNAs were collected from the culture media, and E1A mRNA was quantitated by a quantitative real-time RT-PCR method using E1A primers (Fw: 5'-GAACCACC-TACCCTTCACG-3' (SEQ ID NO: 8), Rev 5'-CCGCCAA-CATTACAGAGTCG-3 (SEQ ID NO: 9)). As a result, it was confirmed that the expression level of E1A mRNA in AdAREF-R was lower than that in AdAREF (FIG. 5).

Figure 6:
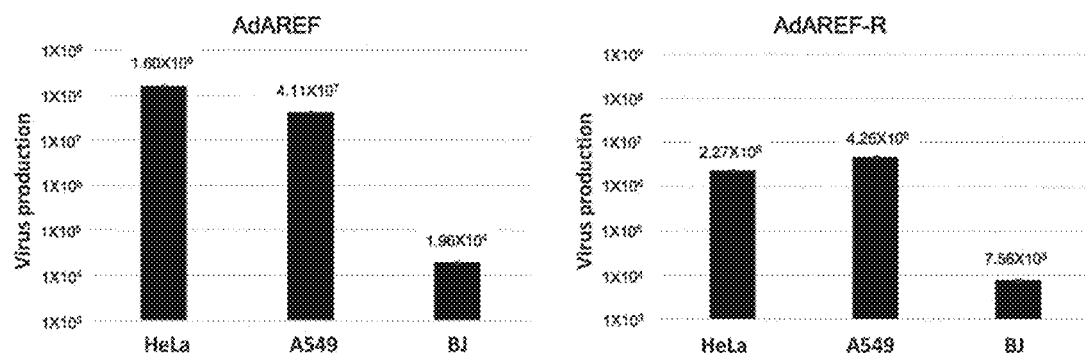
FIG. 6 is graphs illustrating the proliferation potency (virus production) of modified adenovirus AdAREF-R in HeLa, A549, or BJ cells, in comparison with that of control adenovirus AdAREF.

3) Evaluation of Proliferation Potency of Modified Virus in Cancer Cell and Normal Cell $5 \times 10^4$ HeLa cells, $5 \times 10^4$ A549 cells, and $5 \times 10^4$ BJ cells were each inoculated into a 6-well-dish each well of which contained 2-ml DMEM (10%-FBS) and cultured at 37° C. The culture medium was removed, and 2 ml of DMEM containing 10%-FBS was newly added. Furthermore, AdAREF or AdAREF-R prepared in the above-described 1) was added so as to achieve MOI=10, and incubation was performed at 37° C. for 72 hours. After the incubation, viruses were collected from the culture medium, and, by using 293 cells, the amount of the virus was measured by staining hexons in the virus coat component protein by Adeno-X (registered trademark) Rapid Titer Kit (Clontech). As a result, it was confirmed that the proliferation potency of AdAREF-R in a normal cell was lower than that of AdAREF (FIG. 6).

Figure 7:
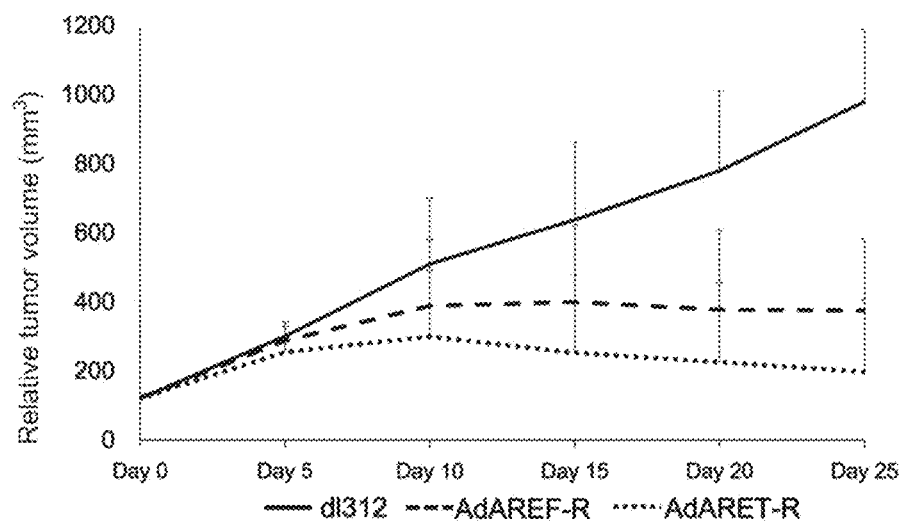
FIG. 7 is a graph illustrating the anti-tumor effect of modified adenovirus AdAREF-R in cancer-bearing mice into which HeLa S3 cells are transplanted, in comparison with that of control adenovirus dl312.

Example 3 Antitumor Effect of Modified Virus in Cancer-Bearing Mouse into which HeLa S3 Cell is Transplanted HeLa S3 cells ($1 \times 10^6$ cells) derived from human cervical cancer were subcutaneously transplanted into 5-week-old nude mice (BALB/c nu/nu; female, n=5) to form tumors. With the day on which the diameter of the tumors was confirmed to become 9 to 10 mm being taken as Day 0, adenovirus dl312 in which the E1A gene is deleted, AdARET-R of Example 1, and AdAREF-R of Example 2 ($1 \times 10^9$ vp; 100 μl) were directly injected to the tumors twice (Day 1 and Day 4), and the volume (mm$^3$, calculated by major-axis×minor axis$^2$×0.5) of the tumors was measured over time. The measurement of the volume of the tumors was started on Day 0 and performed every 5 days. As a result, in both of the groups to which AdAREF-R or AdARET-R were administered, the tumors were substantially prevented from growing, and in vivo effects of both the viruses were confirmed (FIG. 7).

SEQUENCE LISTING

SEQ ID NO: 1 Nucleic acid sequence of modified E4orf6 gene
SEQ ID NO: 2 Amino acid sequence of modified E4orf6 protein
SEQ ID NO: 3 Nucleic acid sequence of ARE in human TNF-α gene
SEQ ID NO: 4 Nucleic acid sequence of insert into pAx-ARETNF or pAx-ARETNF-R
SEQ ID NO: 5 Nucleic acid sequence of enhancer for type 5 adenovirus E1A gene
SEQ ID NO: 6 Nucleic acid sequence of ARE in human c-fos gene
SEQ ID NO: 7 Nucleic acid sequence of insert into pAx-AREFOS or pAx-AREFOS-R
SEQ ID NO: 8 Forward primer for amplifying type 5 adenovirus E1A gene
SEQ ID NO: 9 Reverse primer for amplifying type 5 adenovirus E1A gene

The invention claimed is:

1. A modified adenovirus comprising:
   an E1A gene;
   an E1A enhancer arranged downstream of the E1A gene; and
   an AU-rich element (ARE) introduced into a 3'-untranslated region of the E1A gene or at a position adjacent to the 3'-untranslated region,
   wherein the E1A gene is incorporated so that the transcription direction of the E1A gene is reverse to the direction of the nucleic acid sequence of the E1A enhancer,
   wherein the distance between the E1A gene 5'-end and the E1A enhancer end closer to the E1A gene is 2,900 bp to 3,200 bp, and
   wherein the position adjacent to the 3'-untranslated region is a position that enables a mRNA transcribed from the E1A gene by an RNA polymerase to include the ARE at its 3'-end by the read-through by the RNA polymerase.

2. The modified adenovirus according to claim 1, wherein the modified adenovirus is incapable of expressing a normal E4orf6 protein.

3. The modified adenovirus according to claim 2, wherein the modified adenovirus is an adenovirus modified not to express an E4orf6 protein having an a-helix structure in an oncodomain.

4. The modified adenovirus according to claim 2, comprising a modified E4orf6 gene, the modified E4orf6 gene consisting of a nucleic acid sequence of SEQ ID NO: 1 or a nucleic acid sequence encoding an amino acid sequence identical to an amino acid sequence encoded by the nucleic acid sequence of SEQ ID NO: 1.

5. The modified adenovirus according to claim 2, comprising a modified E4orf6 gene encoding an amino acid sequence of SEQ ID NO: 2.

6. The modified adenovirus according to claim 2, wherein the modified adenovirus is an adenovirus in which E4orf6 is deleted.

7. A medicine for treatment of a disease involving a cell in which stabilization of an mRNA containing an AU-rich element is enhanced, the medicine comprising the modified adenovirus according to claim 1.

8. The medicine according to claim 7, wherein the disease involving the cell in which stabilization of the mRNA containing the AU-rich element is enhanced is a malignant tumor.

9. The modified adenovirus according to claim 1, wherein the E1A enhancer sequence consists of the nucleic acid sequence of SEQ ID No. 5.

10. The modified adenovirus according to claim 1, wherein the nucleic acid sequence as set forth in SEQ ID NO: 4 or SEQ ID NO: 7 is incorporated in a direction reverse to the direction of the nucleic acid sequence of the E1A enhancer.

11. The medicine according to claim 7, wherein the E1A enhancer sequence consists of the nucleic acid sequence of SEQ ID No. 5.

12. The medicine according to claim 7, wherein the nucleic acid sequence as set forth in SEQ ID NO: 4 or SEQ ID NO: 7 is incorporated in a direction reverse to the direction of the nucleic acid sequence of the E1A enhancer.

* * * * *